United States Patent [19]

Jelly

[11] Patent Number: Plant 5,636

[45] Date of Patent: Jan. 14, 1986

[54] ROSE PLANT NAMED JELDANIRAN

[75] Inventor: Robert G. Jelly, Richmond, Ind.

[73] Assignee: E. G. Hill Co., Inc., Richmond, Ind.

[21] Appl. No.: 609,781

[22] Filed: May 14, 1984

[51] Int. Cl.[4] ..... A01H 5/00

[52] U.S. Cl. ..... Plt./26

[58] Field of Search ..... Plt./26

*Primary Examiner*—Robert E. Bagwill

*Attorney, Agent, or Firm*—Charles W. Rummler

[57] ABSTRACT

A new and distinct variety of floribunda rose plant distinguished by its light pink double flowers of medium size which are borne on rigid and strong stems; the plant is well branched and produces from one to four flowers per stem; the flowers are beautifully shaped and are generally of a Venetian Pink color flushed with Neyron Pink; the flowers are long lasting as cut flowers, the petals of which drop off cleanly; and the multiflower florescence of this plant gives it a particular aptitude for forcing for the production of cut flowers.

15 Drawing Figures

BACKGROUND OF THE NEW PLANT

This new rose plant was originated as a seedling at Richmond, Ind., resutling from my crossing of two rose plant varieties selected with the object of producing a strong plant suitable for all uses, particularly for the production of cut flowers. This particular seedling was selected for production because of the beautiful shape and coloration of its flowers, its multiflower production and its apparently vigorous growth habit. Reproduction of this selected seedling was done under my direction at Richmond, Ind., and propagation by budding was carried on through several generations, which demonstrated that the novel characteristics of the new plant would hold true from generation to generation and appeared to be firmly fixed. Plants of this new variety are being grown at Richmond, Ind., and commercial production for the European market is being carried on at Cap d'Antibes, France.

DESCRIPTION OF THE DRAWING

This new variety of floribunda rose plant is illustrated by the accompanying photographic drawing showing in full color distinctive elements of the new plant and in which.

DESCRIPTION OF THE NEW PLANT

Figures 1, 2, 3, 4, 5, 6, 7, 8, 9, 10, 11, 12, 13, 14, 15:
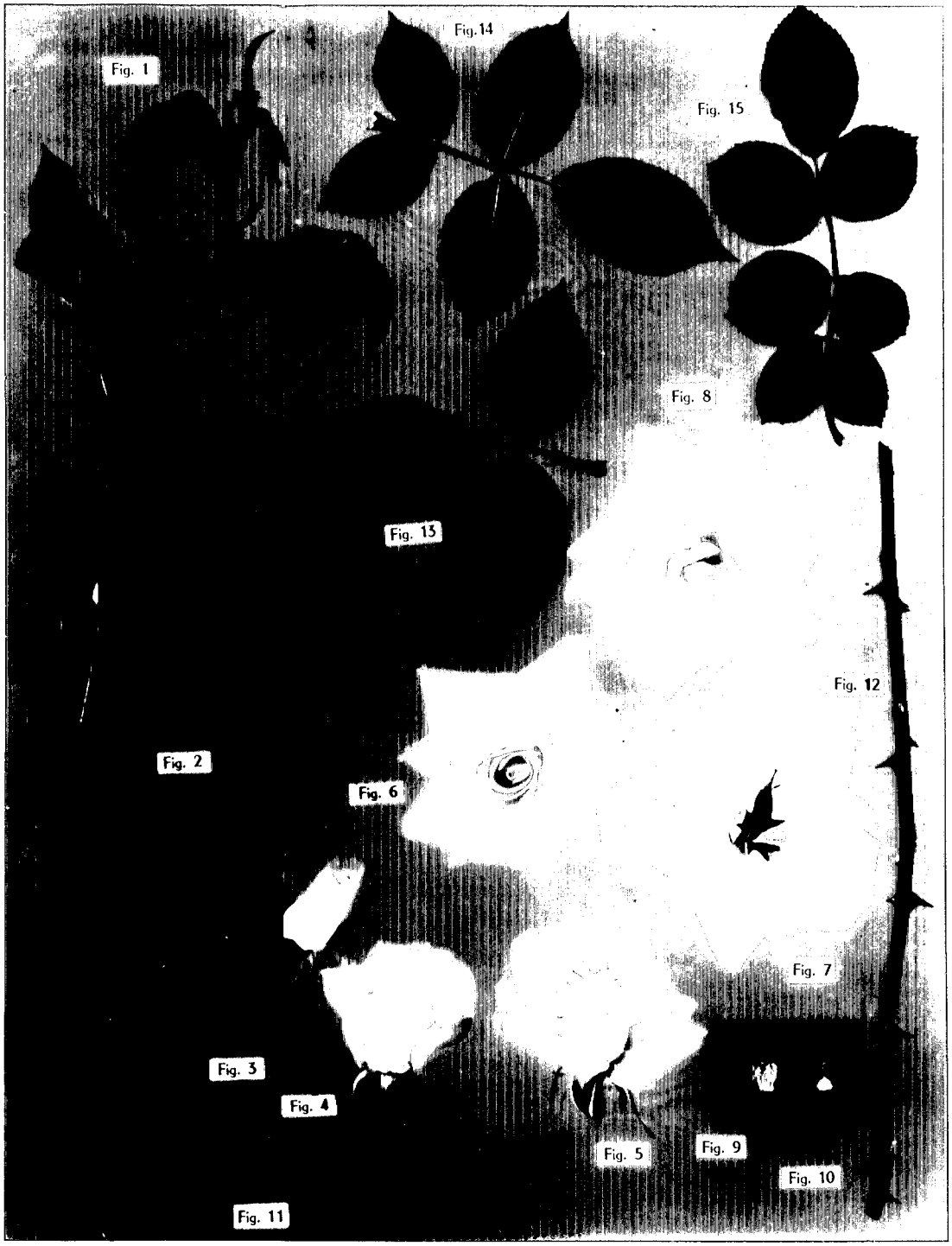
FIG. 1 shows a specimen of a young shoot.
FIG. 2 shows a main stem of the plant bearing buds before opening of sepals for an eleven flower florescence.
FIG. 3 shows a bud when the sepals have opened.
FIG. 4 shows a bud when the petals have opened.
FIG. 5 shows a flower in the course of opening.
FIG. 6 shows a face view of a fully blown flower.
FIG. 7 shows a back or stem-end view of a flower that is fully blown.
FIG. 8 shows a face view of a flower at the end of blowing.
FIG. 9 shows a specimen of receptacle showing the disposition of the stamens (sepals and petals removed)
FIG. 10 shows a specimen of receptacle illustrating the disposition of pistils (sepals, petals and stamens removed)
FIG. 11 shows a portion of mature wood.
FIG. 12 shows a portion of young wood.
FIG. 13 shows a top view of a leaf having three leaflets.
FIG. 14 shows the bottom view of a leaf having five leaflets.
FIG. 15 shows an upper side view of a leaf having seven leaflets.

The following is a detailed description of my new floribunda rose plant as observed on plants being grown in greenhouse at Cap d'Antibes, France, in January, the color designations being according to The R.H.S. Colour Chart of The Royal Horticultural Society at London, England.

THE PLANT

Origin: Seedling.

Parentage:

*Seed parent.*—"Misty Pink" (U.S. Plant Pat. No. 2,945).

*Pollen parent.*—An unnamed variety of unknown origin.

Classification: Floribunda rose plant.

Form: An erect bush.

Height: In general, usually up to about 125 cm. As the result of cutting back of the plants in greenhouse to about 85 cm., the length of the stems to be cut is fixed at about 40 cm. on an average.

Growth: Upright and vigorous.

Branches: Normal.

*Young stems.*—Color: Bronze Green 146A, more or less shaded reddish.

*Mature wood.*—Color: Bronze Green 146A, more solid than young stems and thus appearing darker.

*Prickles.*—Shape: Upper Edge: Straight, slender, slightly inflexed toward the base. Under Edge: Concave. Size: Medium. Quantity: Medium. Color on young stems: Reddish. Color on mature wood: Havana.

Foliage:

*Quantity.*—Medium.

*Form of leaf.*—Odd pinnate.

Leaflets:

*Number.*—3, 5, more often 7 and rarely 9.

*Shape.*—Oval with simple and regular margin, sometimes with a cuneiform base.

*Texture.*—Leathery

*Color.*—Young Foliage: Upper surface — Dark Green 147A. Under surface — Light Green 138B. Adult Foliage: Upper surface — Dark Green 147A. Under surface — Light Green 138B.

*Stipules.*—Adnate, pectinate, fairly wide and linear.

*Petiole.*—Inner surface — Grooved, reddish brown on young leaves, medium green on adult leaves and with more or less glandular edges. Outer surface — Light green, with some small hooked prickles.

THE BUD

Size: Medium.

Shape: Oblong before opening of the sepals.

Length: Average about 3 cm., outside the calyx before opening of the sepals.

Color of petals: On opening:

*Upper surface.*—Crimson 52A, more or less flushed with Neyron Pink 55B on exterior petals.

*Under surface.*—Neyron Pink 55A becoming 55C on exterior petals.

Sepals:

*Inner Surface.*—Tomentous and greenish.

*Under Surface.*—Light green, slightly tomentous. Outside sepals have their edges more or less glandular and slightly appendiculate.

*Character.*—The sepals turn outwardly and downwardly as the bud opens.

Peduncle:

*Length.*—About 6 to 7.5 cm.

*Character.*—Erect and rigid, bearing a few small hooked prickles.

THE FLOWER

Size of bloom: Medium large.

*Diameter.*—About 9 cm. on an average.

Shape: Parallel sides at start of blowing.

*Chorisis.*—Double.

Petalage:

*Number.*—30 on an average.

*Arrangement.*—Imbricated

*Form.*—Rounded, cordiform base; with whitish unguis on both faces.

*Texture.*—Consistent and firm.

*Color.*—In the course of opening; Upper surface — Crimson Pink 52D on inner petals, becoming gradually Venetian Pink 49C flushed with Neyron Pink 55C on the center petals, then French Pink 49D flushed with Neyron Pink 55D on the outer petals. Under surface — Neyron Pink 55B on inner petals becoming 55C, then 55D on outer petals.

Fragrance: None.

Persistence: The petals drop off cleanly.

Lasting quality:

*As cut flowers.*—A relatively long time.

REPRODUCTIVE ORGANS

Stamens:

*Number.*—83 on average.

*Anthers.*—Color: Ochre.

*Filaments.*—Of irregular height, yellow base with ochre top.

Pistils:

*Number.*—52 on average.

*Styles.*—Free, more or less twisted and tomentous. Color: Fuchsine with yellowish base.

Receptacle:

*Color.*—Light green at the dehiscence of the anthers.

*Shape.*—Narrow in longitudinal section and in the shape of a jug.

This new variety of floribunda rose plant has a particularly abundant inflorescence and a vigorous vegetation, it is not particularly affected by sickness, its flowers last long and their petals drop off cleanly.

I claim:

1. A new and distinctive floribunda rose plant, substantially as herein shown and described, particularly distinguished by its abundant inflorescence and its large, double, light pink flowers, a vigorous growth habit, and a good aptitude for forcing.

* * * * *